United States Patent [19]
Cullinan

[11] Patent Number: 5,496,828
[45] Date of Patent: Mar. 5, 1996

[54] METHODS OF INHIBITING ULCERATIVE MUCOSITIS

[75] Inventor: George J. Cullinan, Trafalgar, Ind.

[73] Assignee: Eli Lilly and Company, Indianapolis, Ind.

[21] Appl. No.: 293,790

[22] Filed: Aug. 22, 1994

[51] Int. Cl.$^6$ ............ A61K 31/445; A61K 31/55; A61K 31/40
[52] U.S. Cl. ............ 514/324; 514/212; 514/422
[58] Field of Search ............ 514/324, 212, 514/422

[56] References Cited

U.S. PATENT DOCUMENTS

| | | | |
|---|---|---|---|
| 4,133,814 | 1/1979 | Jones et al. | 514/324 |
| 4,380,635 | 4/1983 | Peters | 514/324 |
| 4,418,068 | 11/1983 | Jones | 514/324 |

FOREIGN PATENT DOCUMENTS

| | | | |
|---|---|---|---|
| WO93/10113 | 5/1993 | WIPO | 514/324 |
| WO93/1074 | 6/1993 | WIPO | 514/324 |

OTHER PUBLICATIONS

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.
Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.
Bryant et al., "Raloxifene is a Tissue Specific Estrogen Agonist", Am Soc. Bone & Min. Res., Tampa, Sep. 18–22, 1993.
Frolick et al., "In Vivo and In Vitro Metabolism of Raloxifene", Am. Soc. Bone & Min. Res., Tampa, Sep. 18–22, 1993.
Glasebrook et al., "Multiple Binding Sites for the Anti-estrogen Raloxifene", Am Soc. Bone & Min. Res., Tampa, Sep. 18–22, 1993.
Hock et al., "Combination of Raloxifene and Human Parathyoid Hormone 1–34, Increased Femur Bone Mass in Young Ovariectomized (OVX) Rats", Am. Soc. Bone & Min. Res., Tampa, Sep. 18–22, 1993.
Sato et al., "DEXA Analysis of Raloxifene Effects on the Bones From Ovariectomized Rats", Am. Soc. for Bone and Min. Res., Tampa, Sep. 18–22, 1993.
Yang et al., "Raloxifene an Anti-Estrogen, Simulates the Effects of Estrogen in Inhibiting Bone Resorption Through Regulating TGFB-3 Expression in Bone;" Am Soc. for Bone and Min. Res., Tampa, Sep. 18–22, 1993.
Black et al., "Distinct, Structure-Related Profiles of Estrogenic and Anti-Estrogenic Activity in the Tamoxifen and LY117018 Series;" The Endocrine Society, Abstract 1982.
Black et al., "Uterine Bioassay of Tamoxifen, Trioxifene, and New Estrogen Antagonist (LY117018) in Rats and Mice," Life Sciences, 26:1980, 1453–1458.
Black et al., "Differential Interaction of Antiestrogens with Cytosol Estrogen Receptors," Molecular and Cellular Endocrinology, 22:1981, 95–103.
Black et al., "Evidence for Biological Action of the Antiestrogens LY117018 and Tamoxifen by Different Mechanisms," Endocrinology 109;1981, 987–989.
Black, L. J. "Biological Actions and Binding Properties of a New Estrogen Antagosist LY117018," In: Homone Antagonists, 129–82, 1982 (M. K. Agarwal ed.) Walter de Gruyter and Co., Berlin New York.
Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Symposium, San Antonio, Texas, Nov. 5–6, 1982.
Black et al., The Antiestrogenic Action of LY139481: Species Uniformity Duration of Action and Kinetics of 3H–LY139481 Distribution In Vivo. Sixty–fifth Annual Meeting of the Endocrine Society, San Antonio, Texas, Jun. 8–10, 1983, abs. 93.
Black et al., Antagonism of Estrogen Action with a New benzothiophene Derived Antiestrogen, Life Sciences, 32:1983. 1031–1036.
Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.
Black et al., Synthesis and Antiestrogenic Activity of [3,4–Dihydro–2(4–methoxyphenyl)–1–napthalenyl] [4–[2–pyrrolidinyl) ethoxyl]–phenyl] methanone, methanesulfonic acid salt, Journal of Medicinal Chemistry 22; 1979, 962–966.

Primary Examiner—Jerome D. Goldberg
Attorney, Agent, or Firm—James J. Sales

[57] ABSTRACT

A method of inhibiting ulcerative mucositis comprising administering to a human in need thereof an effective amount of a compound having the formula

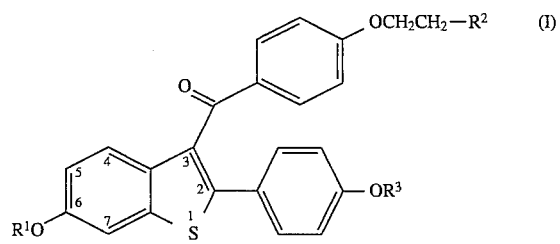

wherein $R^1$ and $R^3$ are independently hydrogen, —CH$_3$,

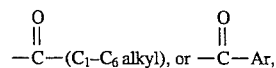

wherein Ar is optionally substituted phenyl;

$R^2$ is selected from the group consisting of pyrrolidine, hexamethyleneamino, and piperidino; or a pharmaceutically acceptable salt of solvate thereof.

5 Claims, No Drawings

OTHER PUBLICATIONS

Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl][4–[2–(1–piperidinyl)ethoxy]–phenyl] methanone Hydrochloride (LY156758), a Remarkably Effective Estrogen Antagonist with Only Minimal Intrinsic Estrogenicity, J. Med. Chem. 27(8), 1984, 1057–1066.

Sonis et al., "Prevention of Chemotherapy Induced Ulcerative Mucositis By Transforming Growth Factor–$\beta 3$", NIH Symposia, May 3, 1994.

METHODS OF INHIBITING ULCERATIVE MUCOSITIS

BACKGROUND OF THE INVENTION

Patients undergoing chemotherapy or radiotherapy for treatment of malignancies are almost invariably faced with moderate or severe side effects due to their therapy. One of the common side effects faced by cancer patients is the induction of ulcerative mucositis of the mucosal membranes. This mucositis is especially prominent in the oral cavity. This side effect, although not as life threatening as other side effects such as anemia or immunosuppression, nonetheless often becomes the dose limiting factor in the continuation of therapy in many cancer patients.

Ulcerative mucositis is marked by the formation of slowly healing open ulcers in the oral cavity causing a great deal of pain and discomfort to the patient. Eating, drinking, and swallowing become difficult and painful and additionally, the salivary glands are often effected compounding the discomfort. The presence of open ulcers in the mouth often lead to opportunistic infections of bacterial, viral, and fungal origin in these patients, who are often immunologically suppressed due to their therapy. These oral infections must be carefully monitored to avoid their spreading to life-threatening, systemic infections.

As yet, there is no treatment for such mucositis except either cessation of the therapy or palliative and supportive interventions. Some of the palliative treatments in current use include the use of antibiotics to reduce the chance of infection, the use of anti-histamines and anti-inflammatory drugs, and the use of pain reducing medications. All of these treatments are either unacceptable, as with the case of cessation of cancer therapy or partially successful in relieving the suffering from the mucositis.

For a more detailed description of radio- and chemotherapy induced mucositis, its treatment, management, and causes see Holland, J. F. et al.; Cancer Medicine, Third Ed., Lea & Febiger, Philadelphia Pa., 1993; Vol.2, Section XL, pp. 2382–2385 and references therein.

The current understanding of the mechanism which causes ulcerative mucositis in cancer patients undergoing radio- or chemotherapy is that both normal mucosal cells and malignant cancer cells share one common property, i.e., these are cells which are rapidly growing or cycling. Normally the mucosal lining turns over at a very rapid rate compared to most other tissue compartments in the body. This rapid mucosal turnover is also shared by several other normal tissues such as cellular blood elements, hair, skin, etc. It is not surprising to find that these tissues are also targets of various cancer therapies, because the governing strategy for the treatment of cancer has been aimed at targeting rapidly proliferated cancer cells by a variety of cellular mechanisms. Thus, cancer drugs which are most effective at interrupting the growth of cancer cells are often the most damaging agents to the normal, proliferating cells in the body, such as the mucosal lining. Other tissue compartments of the body whose cells are not as rapidly cycling, such as muscle and nerve cells, are not as prone to the rapid and deleterious effects of such cancer therapies.

Recently there has been a report in the literature, suggesting that Transforming Growth Factor-β 3 (TGF-β 3) may be useful in treating patients suffering from ulcerative mucositis induced by cancer therapy. The authors hypothesis is that TGF-β 3 slows the rate of turnover of epithelial cells (epithelial cells are the predominant cell type in the mucosal lining) and thus these cells might be spared the effects of the cancer therapy. The authors give experimental data both in cell culture and in animal models which support their hypothesis. (Sonis, et al., Prevention Of Chemotherapy-Induced Ulcerative Mucositis by Transforming Growth Factor-β 3., Abst., NIH Symposia on TGF-βs, Bethesda Md., 3 May 1994).

TGF-β is a peptide growth factor which refers to a generic family of peptides, often called isoforms meaning that members of the family either share amino acid homology and/or have similar physiological actions. Of particular interest to the subject of wound healing are: TGF-βs 1, 2, and 3. For further discussion of the TGF-β family of peptides, the subject is reviewed in: Roberts et al., The transforming growth factor-βs. In: Sporn and Roberts, eds. Peptide growth factors and their receptors I. Berlin: Springer Verlag, 1990: 419–472.

It would seem reasonable that an agent which might slow the rapid rate of turnover of the mucosal lining may be useful in protecting that tissue from the effects of the commonly used cancer therapies.

SUMMARY OF THE INVENTION

This invention provides methods of inhibiting ulcerative mucositis comprising administering to a human in need thereof an effective amount of a compound of formula I

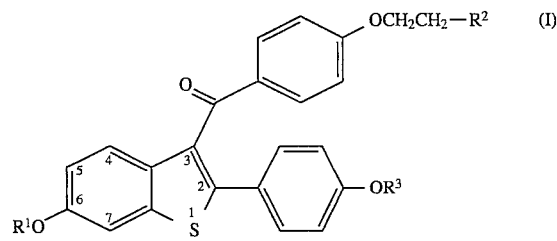

wherein $R^1$ and $R^3$ are independently hydrogen, —$CH_3$,

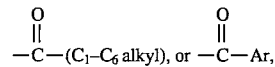

wherein Ar is optionally substituted phenyl;
$R^2$ is selected from the group consisting of pyrrolidino, hexamethyleneimino, and piperidino; and pharmaceutically acceptable salts and solvates thereof.

DETAILED DESCRIPTION OF THE INVENTION

The current invention concerns the discovery that a select group of 2-phenyl-3-aroylbenzothiophenes (benzothiophenes), those of formula I, are useful for inhibiting ulcerative mucositis, particularly induced by chemotherapy or radiotherapy.

The therapeutic and prophylactic treatments provided by this invention are practiced by administering to a human in need thereof a dose of a compound of formula I or a pharmaceutically acceptable salt or solvate thereof, that is effective to inhibit ulcerative mucositis.

The term "inhibit" includes its generally accepted meaning which includes prohibiting, preventing, restraining, and slowing, stopping or reversing progression, severity or a resultant symptom. As such, the present method includes both medical therapeutic and/or prophylactic administration, as appropriate.

Raloxifene is a preferred compound of this invention and it is the hydrochloride salt of a compound of formula 1 wherein $R^1$ and $R^3$ are hydrogen and $R^2$ is 1-piperidinyl.

Raloxifene is a nuclear regulating compound, and has been shown to bind to the estrogen receptor, and was originally thought to be a molecule whose function and pharmacology was that of an anti-estrogen in that it blocked the ability of estrogen to activate uterine tissue and estrogen dependent breast cancers. Indeed, raloxifene does block the action of estrogen in some cells; however, in other cell types, raloxifene activates the same genes as estrogen does and displays the same pharmacology, e.g., osteoporosis, hyperlipidemia, etc. As a result, raloxifene has been referred to as an anti-estrogen with mixed agonist-antagonist properties. The unique profile which raloxifene displays and differs from that of estrogen is now thought to be due to the unique activation and/or suppression of various gene functions by the raloxifene-estrogen receptor complex as opposed to the activation and/or suppression of genes by the estrogen-estrogen receptor complex. Therefore, although raloxifene and estrogen utilize and compete for the same receptor, the pharmacological outcome from gene regulation of the two is not easily predicted and is unique to each.

It has been reported in the literature that part of the pharmacologic action displayed by Raloxifene is due to its ability to induce TGF-$\beta$3. Raloxifene shares this ability with estrogen; however, it appears that raloxifene induces this factor to a greater extent than estrogen.

The compound of formula I would be a useful agent in the inhibition of ulcerative mucositis. This invention is not limited to only the mucositis seen in the oral cavity but also includes other mucosal lining such as found in the intestinal, uro-genital, and nasal tracts.

Generally, at least one compound of formula I is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like, The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b] thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. The term "optionally substituted phenyl" includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, $\beta$-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, sprays, mouth washes, lozenges, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

Lozenges, troches or pastilles are discoid-shaped solids containing the medicinal agent in a suitably flavored base. The base may be a hard sugar candy, glycerinated gelatin, or the combination of sugar with sufficient mucilage to give it form. Troches are placed in the mouth where they slowly dissolve, liberating the active ingredient. The drug involved can be an antiseptic, local anesthetic, antibiotic, anthihistaminic, antitussive, analgesic, or a decongestant.

Troches maybe prepared extemporaneously by the pharmacist. The mass is formed by adding water slowly to a mixture of the powdered drug, powdered sugar, and a gum until a pliable mass is formed. Powdered acacia in 7% concentration gives sufficient adhesiveness to the mass. The mass is rolled out and the troche pieces cut out using a cutter, or else the mass is rolled into a cylinder and divided. Each piece is shaped and allowed to dry before dispensing.

If the active ingredient is heat stable, it may be prepared in a hard candy base. Syrup is concentrated to the point where it becomes a pliable mass, the active ingredient is added, and the mixture is kneaded while warm to form a homogeneous mass. The mass is gradually worked into a pipe form having the diameter desired for the candy piece and the lozenges cut from the pipe and allowed to cool. This is an entirely mechanical operation with equipment designed for this purpose.

If the active ingredient is heat labile, it may be made into a lozenge preparation by compression. The granulation is prepared in a manner similar to that used for any compressed tablet. The lozenge is made using heavy compression equipment to give a tablet which is harder than usual as it is desirable for the troche to dissolve or disintegrate slowly in the mouth. In the formulation of the lozenge the ingredients are chosen which will promote its slow-dissolving characteristics. Compression is gaining in popularity as a means of making troches and candy pieces because of the increased speeds of compression equipment. In cases where holes are to be placed in troches or candy pieces, core-rod tooling is used. Core-rod tooling includes a rod centered on the lower punch around which the troche is compressed in the die cavity. The upper punch has an opening in its center for the core rod to enter during compression. It is evident that maximum accuracy is needed to provide alignment as the narrow punches are inserted into the die.

The particular dosage of a compound of formula I required to inhibit ulcerative mucositis or its symptoms, according to this invention, will depend upon the severity of the condition, the route of administration, and related factors that will be decided by the attending physician. Generally, accepted and effective oral daily doses will be from about 0.1 to about 1000 mg/day, and more typically from about 50 to about 200 mg/day. Such dosages will be administered to a subject in need thereof from once to about three times each day, or more often as needed, and for a sufficient duration, to effectively inhibit ulcerative mucositis.

It is usually preferred to administer a compound of formula I in the form of an acid addition salt, as is customary in the administration of pharmaceuticals bearing a basic group, such as the piperidino ring. For such purposes the following oral dosage forms are available.

Formulations

In the formulations which follow, "Active ingredient" means a compound of formula I.

Formulation 1: Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

Formulation 2: Raloxifene capsule

| Ingredient | Quantity (mg/capsule) |
| --- | --- |
| Raloxifene | 1 |
| Starch, NF | 112 |
| Starch flowable powder | 225.3 |
| Silicone fluid 350 centistokes | 1.7 |

Formulation 3: Raloxifene capsule

| Ingredient | Quantity (mg/capsule) |
| --- | --- |
| Raloxifene | 5 |
| Starch, NF | 108 |
| Starch flowable powder | 225.3 |
| Silicone fluid 350 centistokes | 1.7 |

Formulation 4: Raloxifene capsule

| Ingredient | Quantity (mg/capsule) |
| --- | --- |
| Raloxifene | 10 |
| Starch, NF | 103 |
| Starch flowable powder | 225.3 |
| Silicone fluid 350 centistokes | 1.7 |

Formulation 5: Raloxifene capsule

| Ingredient | Quantity (mg/capsule) |
| --- | --- |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
| --- | --- |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1– 1000 mg of Active ingredient are made up as follows:

Formulation 7: Tablets

| Ingredient | Quantity (mg/tablet) |
|---|---|
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The Active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of Active ingredient per 5 mL dose are made as follows:

Formulation 8: Suspensions

| Ingredient | Quantity (mg/5 ml) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The Active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Formulation 9: Nasal Solution

| Ingredient | Quantity (mg/5 ml) |
|---|---|
| Active ingredient | 0.1–1000 mg |
| Chlorobutanol | 0.5 g |
| Sodium Chloride | 0.5 g |
| Water | to 100 ml |

Formulation 10: Sublingual or Buccal Tablets

Sublingula or buccal tablets, each containing 10 mg of active ingredient, may be prepared as follows:

| Ingredient | Quantity Per Tablet |
|---|---|
| Active ingredient | 0.1–1000 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2– 4 mm. This diffusion matrix is then cut to form individual tablets having the appropriate size.

ASSAYS

ASSAY 1

Five to fifty golden Syrian hamsters are begun on a daily oral dosage regimen of a compound of formula I one week before administering chemotherapy. The oral dosage regiman is continued during the 2 week chemotherapy and two weeks beyond. Positive results against mucositis include reduction of the course and/or severity of the mucositis, as measured by the epithelial BrdU labeling index, the PCNA-positive epithelial cell fraction weights, and/or survival rates.

ASSAY 2

Five to fifty patients are selected for the clinical study. The patients are currently undergoing either chemo or radiotherapy which has induced ulcerative mucositis. Because of the idiosyncratic and subjective nature of these disorders, the study has a placebo control group, i.e., the patients are divided into two groups, one of which receives a compound of formula 1 as the active agent and the other receives a placebo. Patients in the test group receive between 50–200 mg of the drug per day by the oral route. They continue this therapy for the duration of the therapy and 2 months beyond. Accurate records are kept as to the number and severity of the symptoms in both groups and at the end of the study these results are compared. The results are compared both between members of each group and also the results for each patient are compared to the symptoms reported by each patient before the study began.

ASSAY 3

Five to fifty patients are selected for the clinical study. The patients are set to undergo either chemo or radiotherapy which will induce ulcerative mucositis. Because of the idiosyncratic and subjective nature of these disorders, the study has a placebo control group, i.e., the patients are divided into two groups, one of which receives a compound of formula 1 as the active agent and the other receives a placebo. Patients in the test group receive between 50–200 mg of the drug per day by the oral route, being two weeks prior to chemo or radiotherapy. They continue this therapy for the duration of the therapy and 2 months beyond. Accurate records are kept as to the number and severity of the symptoms in both groups and at the end of the study these results are compared. The results are compared both between members of each group and also the results for each patient are compared to the symptoms reported by each patient before the study began.

Utility of the compounds of formula I is illustrated by the positive impact they have in at least one of the assays described above.

I claim:

1. A method of inhibiting radiation or chemotherapy induced ulcerative mucositis comprising administering to a human in need thereof an effective amount of a compound having the formula

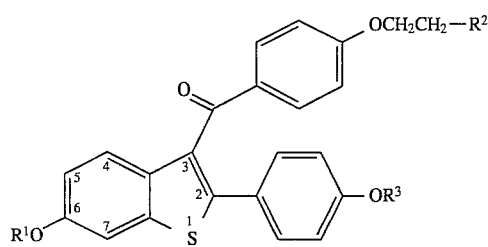

wherein $R^1$ and $R^3$ are independently hydrogen, —$CH_3$,

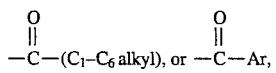

wherein Ar is optionally substituted phenyl;
$R^2$ is selected from the group consisting of pyrrolidine, hexamethylenemino, and piperidino; or a pharmaceutically acceptable salt of solvate thereof.

2. The method of claim 1 wherein said compound is the hydrochloride salt thereof.

3. The method of claim 1 wherein said compound is

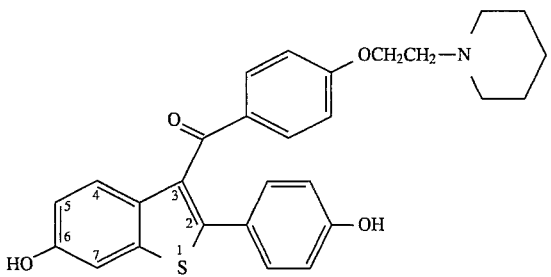

or its hydrochloride salt.

4. The method of claim 1 wherein said ulcerative mucositis is oral.

5. The method of claim 1 wherein said ulcerative mucositis is induced by cancer therapy.

* * * * *